(12) United States Patent
Bunker et al.

(10) Patent No.: US 7,890,274 B2
(45) Date of Patent: Feb. 15, 2011

(54) METHOD FOR QUANTIFYING HOLE FLOW RATES IN FILM COOLED PARTS

(75) Inventors: Ronald Scott Bunker, Waterford, NY (US); Jason Randolph Allen, Niskayuna, NY (US); Jared Michael Crosby, Scotia, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 12/413,756

(22) Filed: Mar. 30, 2009

(65) Prior Publication Data

US 2010/0250155 A1 Sep. 30, 2010

(51) Int. Cl.
*G01N 25/00* (2006.01)
*G06F 19/00* (2006.01)

(52) U.S. Cl. ........................................................ 702/45
(58) Field of Classification Search ...................... 702/45
See application file for complete search history.

(56) References Cited

U.S. PATENT DOCUMENTS

| 3,836,283 | A  * | 9/1974 | Matsuki et al. ............ 416/96 R |
| 4,644,162 | A  * | 2/1987 | Bantel et al. ................. 250/340 |
| 5,111,046 | A  * | 5/1992 | Bantel ......................... 250/330 |
| 6,422,743 | B1 * | 7/2002 | Nirmalan et al. .............. 374/43 |
| 6,585,408 | B2 * | 7/2003 | El-Gabry et al. .............. 374/43 |
| 6,732,582 | B2 * | 5/2004 | Bunker et al. ............. 73/204.21 |
| 7,040,805 | B1   | 5/2006 | Ou et al. |
| 7,388,204 | B2 * | 6/2008 | Key et al. .................... 250/340 |
| 7,651,261 | B2 * | 1/2010 | Bunker et al. ................. 374/43 |
| 7,671,338 | B2 * | 3/2010 | Key ............................. 250/340 |
| 2004/0037344 | A1 * | 2/2004 | Bunker et al. ................. 374/40 |
| 2006/0256837 | A1 * | 11/2006 | Clifton et al. ............... 374/137 |
| 2008/0237466 | A1   | 10/2008 | Key |

FOREIGN PATENT DOCUMENTS

| GB | 2164746 A | 3/1986 |
| WO | 9954692 | 10/1999 |

OTHER PUBLICATIONS

Stefan Friedrichs, Endwall Film-Cooling in Axial Flow Turbines, A Dissertation Submitted for the Degree of Doctor of Philosophy, pp. 1-206, Whittle Laboratory, Cambridge university Engineering Department, Jan. 1997.
EP10157405 Search Report, Aug. 6, 2010.
X. Maldague et al., "Transient Thermographic NDE of Turbine Blades," SPIE vol. 1313, Thermosense XII, 1990, pp. 161-171.

* cited by examiner

*Primary Examiner*—Michael P Nghiem
*Assistant Examiner*—Cindy H Khuu
(74) *Attorney, Agent, or Firm*—Penny A. Clarke

(57) ABSTRACT

A method for measuring a flow rate through a cooling hole of a film cooled part includes the steps of 1) measuring a transient thermal response of an internal surface temperature corresponding solely to an inside portion of a cooling hole for a film cooled part resulting from a flow of fluid through the part, the fluid having an initial temperature that is different from an initial temperature of the film cooled part, 2) mathematically characterizing the transient thermal response, and 3) determining the cooling hole flow rate from the mathematical characterization.

19 Claims, 3 Drawing Sheets

METHOD FOR QUANTIFYING HOLE FLOW RATES IN FILM COOLED PARTS

BACKGROUND

The invention relates generally to film-cooled parts and more particularly to a method for quantifying hole flow rates in film cooled parts.

Gas turbines and other high-temperature equipment use film cooling extensively for effective protection of the hot gas path components, such as turbine blades. Film cooling refers to a technique for cooling a part in which cool air is discharged through a plurality of small holes in the external walls of the part to provide a thin, cool barrier along the external surface of the part and prevent or reduce direct contact with hot gasses.

Accurate knowledge of the film hole flow rates is required to determine how each part should behave compared to the design intent. Inspection of parts to measure these flow rates determines the acceptability of the parts for use, and hence, also has a large impact on cost and rework. Such inspection or measurement can be used to help determine the life or remaining life of a part. Inspection of serviced parts determines their ability to be returned to service.

The standard method for the measurement of film hole flow rates is known as "flow checks". A flow check measures the total flow through a part placed on a test stand. Comparisons to either gauge measurements on good parts and/or analytic models of the flow circuits determines the acceptability. Typically, this process is so time consuming that only overall parts are flow checked, or at best some individual film rows, but never individual film holes. Furthermore, there is no way to distinguish between two parts which may have very different internal thermal performance (heat transfer coefficients), but which flow the same amount and otherwise pass all external dimensional tests.

One technique that overcomes or alleviates the foregoing disadvantages or drawbacks of the prior art is directed to a method for measuring a flow rate in a cooling hole of a film cooled part comprising measuring a transient thermal response of an external surface temperature of the film cooled part near film cooling holes; mathematically characterizing the transient thermal response; and determining the flow rate from the characterization. Although this technique overcomes or alleviates many of the disadvantages described above, it requires knowledge of hole spacing, orientation and shaping as well as precision in consistently locating the same surface points near holes in each part. It would therefore be advantageous to provide a method for quantifying hole flow rates in film cooled parts without the need for precisely and consistently locating the same surface measurement points near holes in each film cooled part or knowledge of hole spacing, orientation and shaping.

BRIEF DESCRIPTION

Briefly, in accordance with one embodiment, a method for measuring a flow rate through a cooling hole of a film cooled part comprises:

measuring a transient thermal response of an internal surface temperature corresponding solely to an inside portion of a cooling hole for a film cooled part resulting from a flow of fluid through the part, the fluid having an initial temperature that is different from an initial temperature of the film cooled part;

mathematically characterizing the transient thermal response; and determining the cooling hole flow rate from the characterization.

According to another embodiment, a method for measuring a flow rate through a cooling hole of a film cooled part comprises:

measuring a transient thermal response of an internal surface temperature corresponding solely to an inside portion of a cooling hole for a film cooled part resulting from a flow of fluid through the part, the fluid having an initial temperature that is different from an initial temperature of the film cooled part;

mathematically characterizing the transient thermal response; and determining a desired thermal response characteristic from the mathematical characterization.

DRAWINGS

These and other features, aspects, and advantages of the present invention will become better understood when the following detailed description is read with reference to the accompanying drawings in which like characters represent like parts throughout the drawings, wherein.

While the above-identified drawing figures set forth alternative embodiments, other embodiments of the present invention are also contemplated, as noted in the discussion. In all cases, this disclosure presents illustrated embodiments of the present invention by way of representation and not limitation. Numerous other modifications and embodiments can be devised by those skilled in the art which fall within the scope and spirit of the principles of this invention.

DETAILED DESCRIPTION

Figure 1:
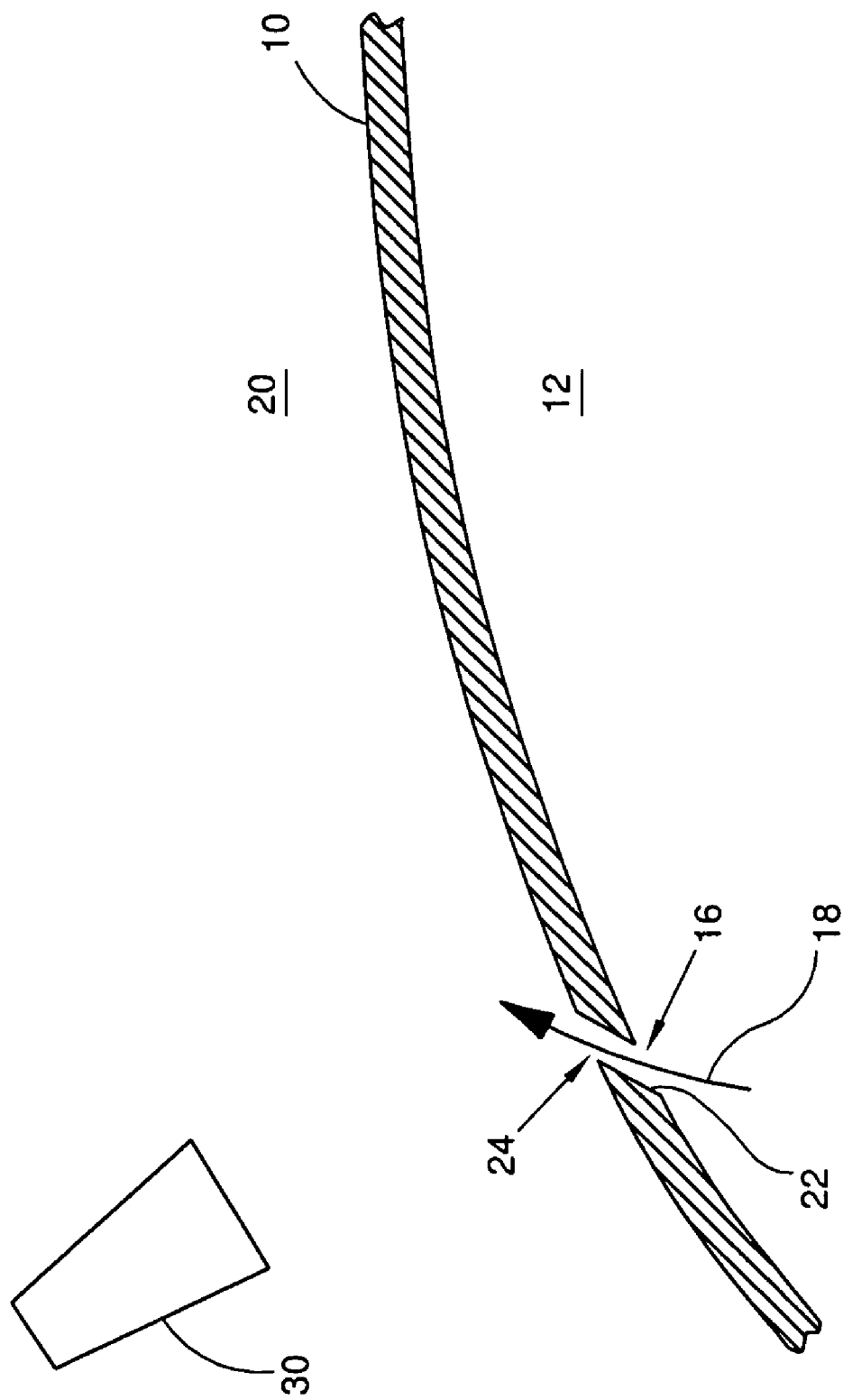
FIG. 1 is a schematic view illustrating a cross section of a portion of a film-cooled part having a film-cooling hole.

FIG. 1 schematically shows a part 10 cooled by a fluid coolant passing through an interior 12 of the part. The fluid coolant may be atmospheric air or another fluid having known thermodynamic properties such as nitrogen. Some of the coolant passes through film-cooling hole 16 along path 18 to an exterior 20 of part 10. Part 10 may have hundreds of such film cooling holes, though only one is shown here for purposes of illustration.

The temperature at various locations on the interior surface 22 of film-cooling hole 16 near the film-cooling hole exit 24 can be measured using infrared detector 30. Infrared detector 30 may be, for example, an imaging infrared radiometer or the like sensitive to electromagnetic radiation of a preselected wavelength. In practice, any wavelength value or range may be used for any material as long as the calibration is done consistently, but one would need to deal with possible issues of signal strength or sensitivity to other factors. If the emissivity is unknown, then an additional step to determine this value must be added.

Coolant film hole 16 along path 18 generates a large heat transfer coefficient between the coolant and the inside walls 22 of coolant film hole 16, generating a localized cooled zone within coolant film hole 16. Note that this creates a heat sink locally which then conductively removes more heat from surrounding material. It will be understood that these heat transfer effects are described for the case where the part is at a higher temperature than the fluid coolant, and that similar effects will occur when the coolant is at a higher temperature than the part, except that the heat will be transferred into the part instead of out of the part.

In practice, the flow rate through a coolant film hole will induce a total material field thermal response when the fluid is at a different temperature than that of the material. In the present methodology embodiments, this becomes a transient thermal response when, for example, a cooler fluid such as air is flowed through the component and the coolant film holes 16. The material defining the coolant film hole 16 is then cooled from the initial temperature of the part 10 to the coolant temperature over a period of time. The material thermal transient data, and specifically the surface temperatures solely inside the coolant film hole exits 24, as a function of time, are used herein to deduce the flow rate through each coolant film hole 16.

The present inventors discovered that accurate, reliable and repeatable detection and measurement of mass flow rates through coolant film holes can be characterized via thermal transient responses associated solely with the surface 22 inside the hole exits 24. More specifically, they discovered that measurement of flow rate through each individual coolant film hole 16 can be determined from only the material temperature response immediately inside a corresponding coolant film hole exit 24, as determined for example, by an infrared device 30, and even when factors such as hole spacing, orientation and shaping are not employed; and that only the simplest possible thermal decay, or thermal buildup response may be required to achieve the desired measurement results. The methodology embodiments described herein advantageously eliminate the need for precision in consistently locating the same surface points near holes in each part when determining film hole flow rates via thermal transient responses, and allows easy detection of measurement (film hole) locations via automation and computer recognition systems. According to one aspect of the invention, an optimized process window is clearly defined by set-point limits on the hole pressure ratio time-response and the internal coolant film hole exit surface temperature-time gradient response.

Note that it is not required to view the same location inside each film hole in a part, nor even precisely the same location inside a common film hole from part-to-part. By use of the interior hole surface, this thermal response is so heavily dominated by the internal heat transfer coefficient that the method is insensitive to such location changes. Recognize that "location" means a single detected point, or a group of detected points, processed to obtain surface temperature.

The relationship of the coolant film hole flow rate to this thermal transient is of the form:

Film hole flow rate=f (hole pressure ratio time-response, internal film hole exit surface temperature-time gradient response).

Figure 2:
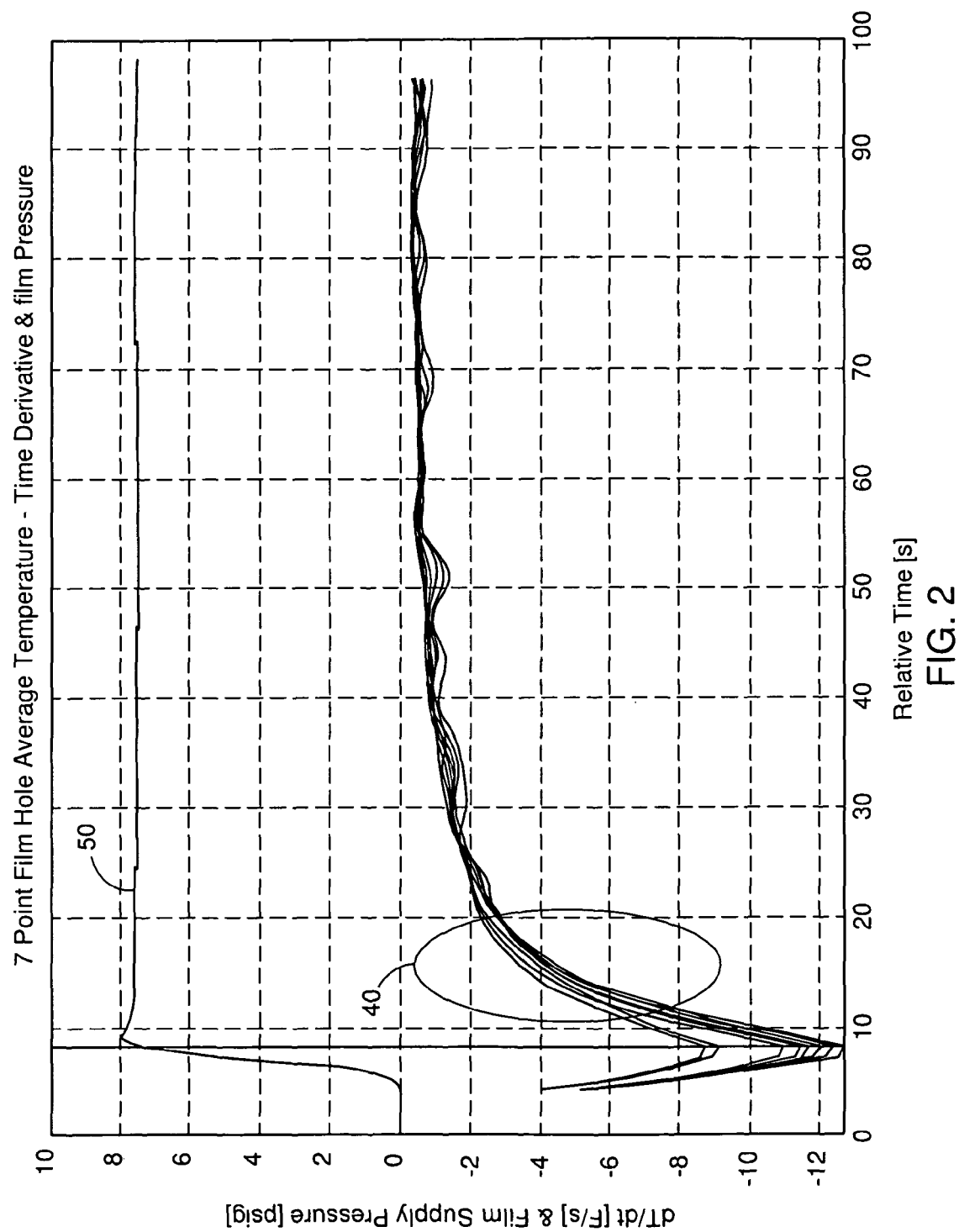
FIG. 2 is a graph illustrating thermal transient data for a plurality of film-cooling holes subjected to identical pressure ratio conditions.

FIG. 2 is a graph illustrating thermal transient data for a plurality of film-cooling holes (enumerated 16 in FIG. 1) in which each hole is subjected to an identical pressure ratio condition of 1.5 to generate a plurality of temperature response curves 40. Pressure ratio as used herein means the ratio of absolute pressure inside a film-cooling hole 16 as compared to an absolute pressure outside the film-cooling hole 16. If for example, the absolute pressure inside the film-cooling hole 16 is 20 psi, and the pressure outside the film-cooling hole 16 is 15 psi (or about atmospheric pressure), then the pressure ratio is 20/15 or 1.333. According to one aspect, the temperature response curves 40 may be non-dimensionalized to normalize all response curves 40 to a common basis.

According to one embodiment, a comparative technique is employed to determine a film-cooling hole flow rate. This comparative technique utilizes a standard test part, sometimes referred to as a "gold standard", that may be configured with a plurality of film-cooling holes and that is first tested by subjecting the standard test part to a series of coolant flow conditions corresponding to different film hole pressure ratios. The transient thermal response for a desired film hole is measured at each of the film hole pressure ratios and then is characterized mathematically. The resultant mathematical characterizations are then used to generate a calibrated film hole flow rate map (response). FIG. 2 illustrates a plurality of transient thermal responses 40 associated with a film-cooling hole that is subjected to a film supply pressure 50.

Film-cooling hole flow rate(s) associated with subsequently manufactured parts are determined as a function of the foregoing mathematically characterized transient thermal responses simply by correlating a measured thermal response characteristic to the calibrated film hole flow rate map using film-cooling hole data from a film-cooling hole in a hole location corresponding to the same hole location as in the standard test part.

A calibration map according to one aspect is determined empirically. Alternatively, numerical predictions such as by computational fluid dynamics and/or finite element analyses could be used in place of or in combination with experimental data to determine the thermal transient response calibration map without experimentation. In practice, the numerical method would be calibrated with experimental data; but this may require far fewer test points than would be necessary to develop calibration factors derived entirely from experimental data. The term "calibration factor" is used loosely herein to refer to a relation between the transient thermal response characteristic(s) and film-cooling hole flow rate(s); in which this relation may in fact be a non-linear function.

Once the transient response curve 40 is obtained for a particular exit hole 16, the flow rate is determinable from a mathematical characterization of curve 40, e.g. from the relative locations of specific points on curve 40. The flow rate through a particular film-cooling hole 16 may be determined, for example, as a function of the magnitude of temperature recovery R, which is the difference that occurs between a first time $t_1$ and a second time $t_2$ on curve 40 according to one embodiment. Alternatively, the flow rate may be determined, for example, from the length of recovery time or difference in slopes at different points on curve 40. The relation between recovery R, recovery time, or difference in slopes and the flow rate through film-cooling hole 16 may be determined empirically, through numerical analysis, or a combination thereof as discussed above. According to one aspect, the mathematical characterization is an exponential curve having the form $Ae^{-Bt}$, where the coefficient B correlates to the flow rate.

This technique for measuring film hole flow rates can be calibrated for film-cooling holes on a test bench, and thus the calibration may be done once for all parts and all uses. Individual film-cooling hole inspection and flow rate measurements can be made.

According to one embodiment, a temperature response curve 40 at a particular film-cooling hole 16 pressure ratio is obtained via taking a single snapshot of the internal surface of the film-cooling hole 16 using an infrared camera. The snapshot reveals the temperature at each of several pixel locations that can then be used to construct the corresponding temperature response curve 40 at the selected pressure ratio.

Figure 3:
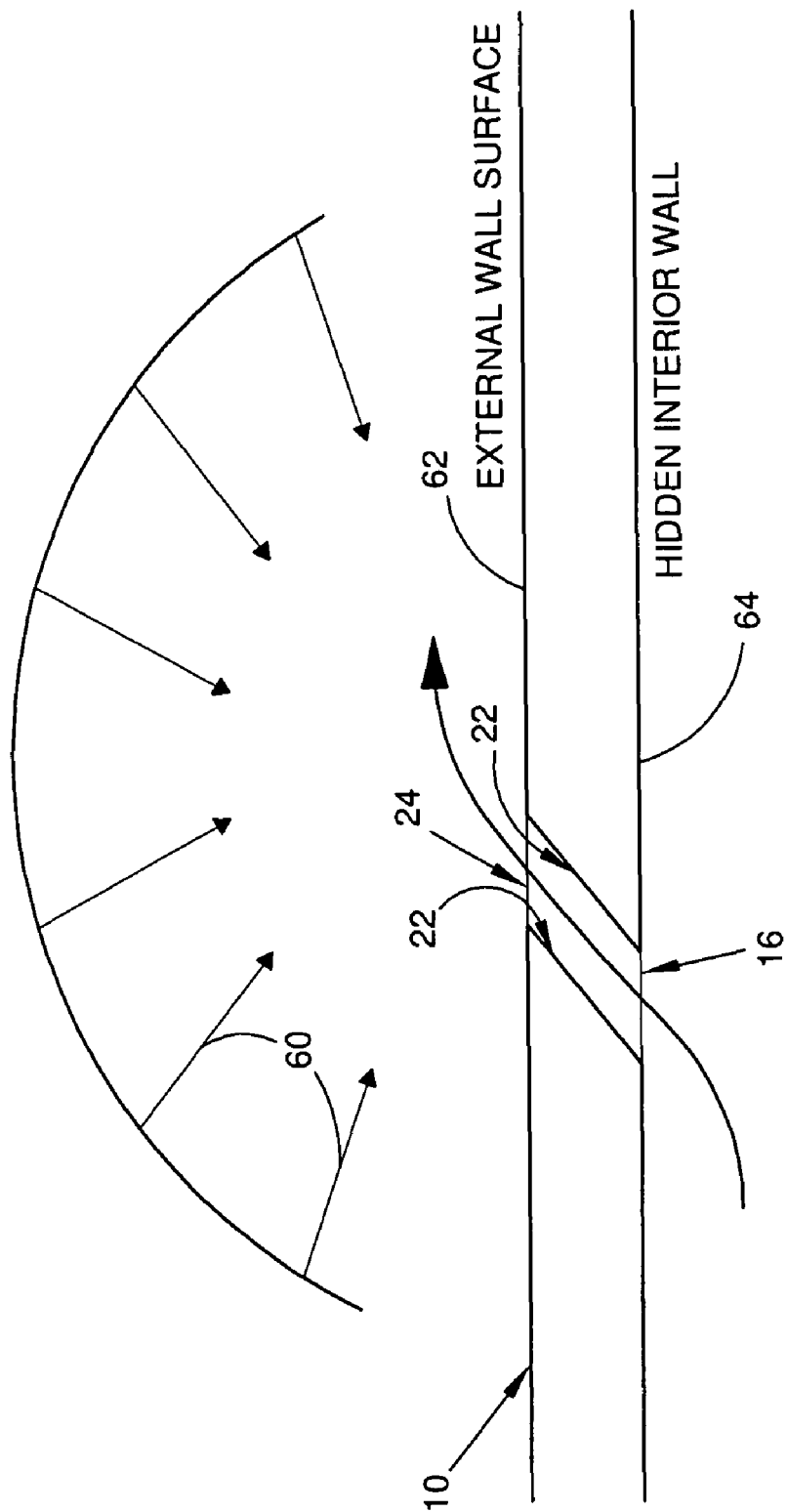
FIG. 3 is a diagram depicting lines of sight viewing of the interior surface(s) of the film-cooling hole depicted in FIG. 1 from any accessible direction according to one embodiment.

FIG. 3 is a diagram depicting lines of sight 60 viewing of the interior surface(s) 22 of a film-cooling hole 16 from any accessible direction. The lines of sight 60 can be from any accessible direction, not only normal to the surface 62 of the part 10. Note FIG. 3 is two-dimensional, and the actual film-cooling hole 16 is three-dimensional.

With continued reference to FIG. 3, internal surface 22 means any viewable portion of the interior or the film-cooling hole 16, not the external wall surface 62, nor the hidden interior wall 64. In practice, the viewable surface is that surface nearer the hole exit 24. Note that in FIG. 3, hole exit 24 is actually the imaginary or notional flow exit plane at the surface 62, not a real physical surface. More specifically, hole exit 24 is the flow exit plane as extended from the surrounding part external surface 62 and not any portion of the actual surface 22 inside the hole 16. Thus, although this exit plane cannot be seen in practice, the surface 22 is inside the hole exit 24.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for measuring a flow rate through a cooling hole of a film cooled part, the method comprising:
   passing a fluid coolant through a film cooled part cooling hole such that a heat transfer coefficient is generated between the coolant and the inside walls of the cooling hole to generate a localized cooled zone within the cooling hole;
   measuring a transient thermal response of an internal surface temperature corresponding solely to an inside portion of the cooling hole for the film cooled part resulting from the flow of fluid through the part, the fluid having an initial temperature that is different from an initial temperature of the film cooled part;
   mathematically characterizing the transient thermal response;
   determining the cooling hole flow rate from the characterization;
   determining if the film cooled part is useable or reworkable based upon the determined cooling hole flow rate and the mathematical characterization; and
   reworking the film cooled part cooling hole to achieve a desired flow rate and transient thermal response when the determined cooling hole flow rate and the mathematical characterization indicates the film cooled part cooling hole ability to be put into service.

2. The method of claim 1, wherein measuring comprises using at least one of mid-infrared detection and longwave infrared detection.

3. The method of claim 1, wherein measuring comprises measuring a transient thermal response of a point on an interior surface of the cooling hole near the cooling hole exit.

4. The method of claim 1, wherein mathematically characterizing includes fitting an exponential curve to measurements generated from measuring the transient thermal response.

5. The method of claim 1, wherein said determining comprises applying a calibration factor to the mathematical characterization to obtain the flow rate.

6. The method of claim 1, wherein the initial temperature of the fluid is different than the initial temperature of the part.

7. The method of claim 1, wherein the fluid is atmospheric air.

8. The method of claim 1, wherein measuring comprises: commencing the flow of fluid;
measuring the surface temperature at one or more points within the exit of the cooling hole of the part at or subsequent to pressure stabilization of the flow of fluid and prior to stabilization of the surface temperature.

9. The method of claim 8, wherein the characterization comprises a relationship between the measurements of the surface temperature.

10. The method of claim 8, wherein the characterization comprises a recovery time, the recovery time being an amount of time that it takes for temperature gradients within the cooling hole to dissipate, wherein the flow rate is determined as a function of the recovery time.

11. The method of claim 10, wherein the temperature gradients are determined to be dissipated when a rate of change of the surface temperature reaches a threshold.

12. A method for measuring a flow rate through a cooling hole of a film cooled part, the method comprising:
   passing a fluid coolant through a film cooled part cooling hole such that a heat transfer coefficient is generated between the coolant and the inside walls of the cooling hole to generate a localized cooled zone within the cooling hole;
   measuring a transient thermal response of an internal surface temperature corresponding solely to an inside portion of a cooling hole for a film cooled part resulting from a flow of fluid through the part, the fluid having an initial temperature that is different from an initial temperature of the film cooled part;
   mathematically characterizing the transient thermal response;
   determining a thermal response characteristic from the mathematical characterization;
   determining if the film cooled part is useable or reworkable based upon the determined thermal response characteristic and the mathematical characterization; and
   reworking the film cooled part cooling hole to achieve a desired thermal response characteristic and transient thermal response when the determined thermal response characteristic and the mathematical characterization indicates the film cooled part cooling hole ability to be put into service.

13. The method of claim 12, further comprising comparing the desired thermal response characteristic to a corresponding thermal response characteristic associated with a standard film cooled part and determining the flow rate there from.

14. The method of claim 12, wherein the desired thermal response characteristic comprises a magnitude of temperature recovery occurring between a first time $t_1$ and a second time $t_2$ based on the mathematical characterization.

15. The method of claim 12, wherein the desired thermal response characteristic comprises a difference in slopes at different points based on the mathematical characterization.

16. The method of claim 12, wherein the desired thermal response characteristic comprises a length of recovery time based on the mathematical characterization.

17. The method of claim 12, further comprising determining the flow rate based on the desired thermal response characteristic using empirical methods.

18. The method of claim 12, further comprising determining the flow rate based on the desired thermal response characteristic using a combination of empirical and numerical methods.

19. The method of claim 12, wherein mathematically characterizing includes fitting an exponential curve to measurements generated from measuring the transient thermal response.

* * * * *